United States Patent [19]

Kaufman et al.

[11] Patent Number: 4,516,970
[45] Date of Patent: May 14, 1985

[54] MEDICAL DEVICE

[76] Inventors: Jack W. Kaufman, 357 Frankel Blvd., Merrick, N.Y. 11566; Donald E. Gardner, 89, The Helm, East Islip, N.Y. 11730

[21] Appl. No.: 417,695

[22] Filed: Sep. 13, 1982

[51] Int. Cl.³ ............................................. A61M 25/00
[52] U.S. Cl. ..................................... 604/270; 128/658
[58] Field of Search ................................ 604/265–270, 604/280; 128/656–658

[56] References Cited

U.S. PATENT DOCUMENTS

| | | | |
|---|---|---|---|
| 2,685,289 | 8/1954 | Devine | 604/270 |
| 3,189,031 | 6/1965 | Andersen | 604/270 |
| 3,566,874 | 3/1971 | Shepherd et al. | 604/265 |
| 3,861,396 | 1/1975 | Vaillancourt et al. | 604/265 X |
| 4,182,342 | 1/1980 | Smith | 604/270 X |

*Primary Examiner*—Dalton L. Truluck
*Attorney, Agent, or Firm*—Peter K. Kontler

[57] ABSTRACT

A medical device, such as a catheter or feeding tube, has a tube element to the front end portion of which a weighted bolus tip is connected. The bolus tip may have a lumen provided with an open front end and communicating with the lumen of the tube, or it may be of solid cross-section in which case outlet openings for the fluid passing through the device are so positioned that it is impossible for a stagnating pool of the fluid to form in the device (to avoid the growth of micro-organisms). The tip itself is produced by mixing powdered metal with a synthetic plastic binder; the mixture is then given the desired shape by casting or molding and thereafter is polymerized to convert the shaped body into a unitary element having no free metal. This renders it impossible for any of the metal powder to spill.

26 Claims, 7 Drawing Figures

MEDICAL DEVICE

BACKGROUND OF THE INVENTION

The present invention relates to a medical device.

More particularly, the invention relates to a medical device in the nature of a tube having a weighted tip or front end portion.

Still more specifically, the invention relates to a medical device of the kind used as catheter, feeding tube or the like.

The invention relates also to the tip—especially a bolus tip—and the composition of the same, which is used as part of the device. It will and should be understood, however, that certain details of the tip are themselves considered to be inventive, independently of the presence or absence of a tube.

There is a host of medical applications in which a tube must be inserted into and through a body orifice, usually to administer a flowable substance such as food or, as is becoming more prevalent, fluids which were heretofore administered by IV (i.e. intravenously).

In many instances, the insertion of such a tube is not possible without—or is at least facilitated by—the presence of a weighted tip or front end portion, generally known as a bolus tip. However, helpful and necessary as the presence of such a tip may be, it has created certain serious problems in the prior art.

One of these problems results from the relationship between tip and tube. The prior-art tips are of solid cross-section and the tube has one or more ports or openings rearwardly of the tip; the fluid exits through these openings. Because the tip is secured to the tube by means of a connector, the openings cannot be located directly adjacent its rear end; this means that there is a length of tube between the rear end of the tip and the outlet openings, in which some of the fluid can accumulate and stagnate (since there is no flow in this tube length). In many instances the nature of the fluid being administered through the tube is such that the fluid constitutes a nutrient medium for the growth of bacteria, and this is precisely what takes place in the "pocket" of tubing filled with the stagnant fluid. It goes without saying that this can be very dangerous, in view of the ever-present possibility that it may lead to serious infection in the patient who is being treated with the device.

Another problem resides in the composition of the prior-art tips themselves. Many of them are rigid and therefore present difficulties in connection with their introduction into a body orifice. More importantly, however, problems are experienced with the kinds of metals of which the prior-art tips are made which are, in fact, flexible to some degree. In order to achieve such flexibility, the metal is used in particulate form; it is even known to use mercury. The metal is then either contained in this form in a lumen of the tip cover, or is simply encased by such a cover (e.g. in the form of a sheath of synthetic plastic material). A problem with this type of construction is that in practice it has been found to leak or spill. That is to say, it has been found that in the prior art there is a tendency for the particulate or fluent metal to escape from its confinement. Should this occur inside a patient, the very least that would happen is the undesirable contamination of a given body region with the spilled metal. Depending upon the kind of metal involved, however, there may also be a greater or lesser toxicity (e.g. mercury) with consequent endangerment of the patient's health.

Also, the prior-art devices require connectors which join the tip to the tube. Aside from the fact that the use of such connectors increases the cost of these devices, since it represents the use of an additional component and the operating step required to install the same, there is the further problem that each such connector potentially represents a situs at which metal spillage may occur.

The prior-art devices are thus clearly in need of improvement which, however, has not heretofore been forthcoming.

OBJECTS AND SUMMARY OF THE INVENTION

An object of the invention is to provide an improved medical device of the general type under discussion, which is not possessed of the prior-art disadvantages.

Another object of the invention is to provide a device of the kind under discussion, which has a novel weighted tip which is both safe and efficacious.

A concomitant object of the invention is to provide such a device wherein the construction of the tip eliminates the possibility of pooling and stagnating (with consequent colonization of microorganisms) of flowable substance being administered through the device.

Still another object of the invention is to provide a device of the character under discussion, which eliminates the leaking or spilling of metal from the weighted tip.

A further object of the invention is to provide such a medical device in which the need for connectors serving as an attachment site between the weighted tip and the tube, is eliminated.

A concomitant object of the invention is to provide an improved weighted tip element per se, i.e. a tip element which overcomes the disadvantages associated with analogous elements of the prior art.

An additional object of the invention is to provide such an improved tip element which is radio-opaque so that its specific location and orientation may be readily imaged (e.g. by means of X-rays or the like) when the element has been introduced into the body of a patient.

Yet another object of the invention is to provide such a tip element which may have a central channel or passage (lumen) or may be of solid cross-sectional area.

Still further objects of the invention are to provide such an improved tip element which is flexible to an extent that does not exist in the prior art, which is cast or molded from a mixture of metal powder and synthetic plastic binder that is thereafter polymerized, and which eliminates the need for connectors at its junction to a tube.

In keeping with these objects, and with still others which will become apparent hereinafter as the description proceeds, one feature of the invention resides in the provision of a medical device such as (but not limited to) a catheter or enteral feeding tube. Briefly stated, such a device may comprise a tube having a passage, a trailing end portion that is adapted to receive a flowable substance, and a leading end portion. The tube may be transparent or at least translucent, in the event it is desired to visually observe the flow of substance through it. Weighting means are provided at the leading tube end portion and, according to the invention, may comprise a (tip) element composed of a mixture of powdered metal and synthetic plastic binder for the metal;

the tip element may be produced by casting or molding, whereupon the plastic binder is polymerized so that the mixture is firmly set as a solid body which may have a lumen or be of solid cross-sectional area. Finally, the device also comprises outlet means for egress of the flowable substance from the tube passage.

In a device constructed in accordance with the invention, all fluids pass through the entire device (i.e. through the tube as well as through the tip), since the channel or lumen in the tip becomes an extension of the passage or lumen in the tube. The flowable substance issues from the open front end of the channel in the tip (additional outlet holes may optionally be provided in the sidewall of the tip and/or in the tube rearwardly of the tip), thus completely eliminating any "pocket" in which flowable substance might otherwise accumulate and stagnate. This eliminates or at least minimizes the colonization of microorganisms.

The tip may be provided with a flexibility-enhancing feature. In particular, the purpose of such a feature would be to make it possible to use a structurally strong tip and one which has a substantial quantity of metal in it to produce whatever weight is desired for a given application, while yet endowing the tip with improved flexibility.

As mentioned before, the tip may be molded or cast from a mixture of particulate metal and a synthetic plastic binder for the same. The formed and then polymerized (bolus) tip according to the invention obviates the need for a prior-art distal tip to contain metals in other, non-bound structural configurations. Moreover, according to the invention it is currently preferred to use the metal in pulverulent form, rather than in form of larger particles (i.e. pellets, pieces or the like), since a better and more uniformly polymerizable mixture results from this. Since polymerization converts the shaped quantity of mixture into a unitary body in which the metal is embedded in the polymeric material, rather than being contained in a space or chamber as in the prior art, the danger of the metal "leaking" or "spilling" from the tip is eliminated.

The tip according to the present invention may be covered or coated with any substance known for this purpose from the prior art, to prevent any possibility of "leaching" of the metal and/or to cover flash or other features normally associated with a molded element.

If the tip is provided with a channel or lumen that is made to communicate with the passage or lumen of the tube, then egress holes for the flowable substance may be eliminated from the tube or, as mentioned before, they may optionally still be provided in the tube and/or even in the sidewall of the tip itself.

The weight of the inventive tip can, of course, be regulated by the kind and quantity of materials used in its construction, especially the kind and quantity of metal, and the length of the finished tip. Furthermore, the smaller the particle size of the metal powder, the heavier the tip will be per unit volume, since the metal particles will be more densely packed in the metal/-binder mixture and leave fewer and smaller interstices for the lighter synthetic plastic binder.

To facilitate its insertion into a body orifice or the like, the tip may be coated with any known-per-se hydrophilic material.

As suggested earlier, the tip according to the invention may, but need not have a channel or lumen. It can also be of solid cross-sectional area and will then still have many of the above-enumerated advantages over the prior art. However, should the tip indeed have such solid cross-sectional area, then the tube itself must be provided with outlet openings for the flowable substance and these should be placed as close as possible to the rear end of the tip to prevent pooling and stagnating of the flowable substance. It is currently preferred to locate the egress holes such that they are formed in a region in which the tube overlaps and grips the rear end of the tip, with the hole or holes passing through the tube wall and in part penetrating into the solid cross-section of the tip; of course, the hole must then also be open to the rear end face of the tip, since this is the only way in which it can communicate with the passage of the tube. This is a positive way of eliminating pooling of the flowable substance, despite the fact that the tip is of solid cross-sectional area.

As already indicated the invention relates not only to a novel medical device overall, but also to the tip element per se, i.e. independently of any other components of the medical device. In addition, the invention also relates to a method of making this tip element, which method assures that the tip element has no free (unbound) metal which might spill from the element, as has been observed in the prior art.

The novel features which are considered to be characteristic of the invention are set forth in particular in the hereto appended claims. The improved device itself, however, together with details of its construction and the best mode of operation currently known to applicant, as well as additional features and advantages of the device and of the method, will be best understood upon a perusal of the following detailed description of specific although purely exemplary embodiments with reference to the accompanying drawing.

DESCRIPTION OF PREFERRED EMBODIMENTS

The present invention will be best understood by comparison with the prior art. Accordingly, a typical example of a prior-art device is therefore illustrated in FIG. 1 and will hereafter be briefly described.

Figure 1:
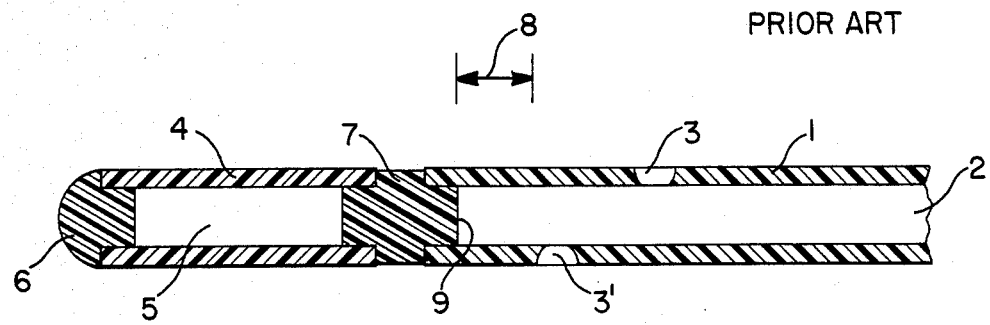
FIG. 1 is a longitudinal section through a prior-art device.

The prior-art feeding tube in FIG. 1 has a tube element 1 provided with a passage or lumen 2. Rearwardly of its front end the tube element 1 is provided with one or more outlet openings 3, 3' for a flowable medium that is admitted through the rear end (not shown) of the tube element. Connected to the front end of the tube element 1 is a weighted tip element 4 of tubular shape, having a lumen as shown. The front end of the lumen in tip element 4 is closed off by a plug 6, the rear end by a connector 7 which also closes off the front end of the lumen 2 in tube element 1 and, of course, as the drawing shows and the name implies, connects the tip element 4 to the tube element 1. The lumen in tip element 4 is thus closed at both ends and forms a chamber 5. In accordance with the prior art, this chamber contains the metal needed for weighting the element 4. The prior art provides several different ways of effecting such weighting, which is to say that the chamber 5 may be filled with mercury, with a charge of metal powder, with metal spheres or with elongated metal slugs.

This device has the disadvantages mentioned earlier herein. Should the plug 6 or the connector 7 become detached from the element 4, as has been found to happen in the prior-art devices, then the metal in chamber 5 is free to spill out of the same. It is self-evident that if this happens while the device is installed in situ in a patient, the consequences may be extremely serious. The other major disadvantage of this device is the "pooling" of liquid that takes place, i.e. the formation of a stagnant pocket of liquid in which bacteria can grow. This can occur because there is a space—designated with reference numeral 8—between the rear end face 9 of connector 7 and the closest outlet opening 3' into which fluid can flow, but from which it cannot flow out again. Depending upon the type of fluid (which acts as a nutrient medium) and the micro-organisms involved, the growth of such organisms can be very rapid. When one adds to this the fact that devices of the kind in question are often left in place for prolonged periods of time, it becomes clear that the growth of such micro-organisms in the stagnant pool of liquid in space 8 can, indeed, represent a very significant danger to the health of a patient.

These problems are all overcome by the present invention.

Figure 2:
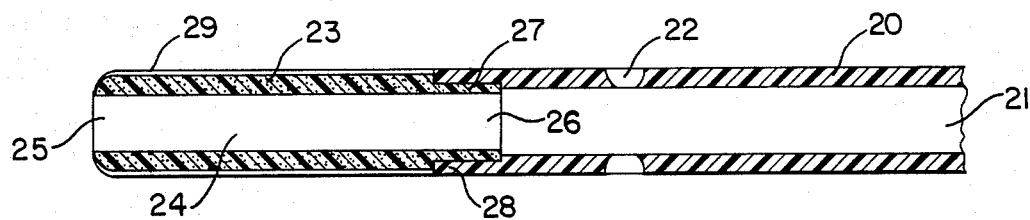
FIG. 2 is a view similar to that in FIG. 1, but illustrating an embodiment of a device according to the present invention.

One device embodying concepts of the invention is illustrated in FIG. 2, where it will be seen to have a tube 20 provided with a passage or lumen 21. The tube may be of natural or synthetic rubber, or of synthetic plastic material; of course, whatever material is used must be medically inert. If desired, and if the type of material permits, the tube 20 may be transparent or at least translucent to permit visual observation of the fluid flow through it, inspection for obstructions, and the like. Tube 20 may—but need not—have outlet openings 22 corresponding to the openings 3, 3' of the prior art.

Secured to the front end portion of tube 20 is a weighted tip element (bolus tip) 23 which, in accordance with the invention, has a longitudinally extending channel or lumen 24 provided with an open front end 25 and a similarly open rear end 26. In other words—and as clearly shown in the drawing—the lumen 24 becomes an extension of the lumen 21 when the element 23 is secured to the tube 20. The two lumens then together in effect constitute a single flow-passage from which the flowable substance admitted at or in the region of the rear end of tube 20 (not shown) issues at the outlet end 25 (and also via the openings 22 if those are optionally provided).

This completely eliminates the problem of pooling, i.e. of the formation of a stagnant pocket of flowable substance, since there is quite literally no space and no way in which such a pocket could form in the inventive device. There is of course no need to explain that if there cannot be any pocket of flowable substance, then there will be no micro-organism growth problem and this danger to the health and well-being of patients is eliminated.

Likewise, the invention eliminates the problem of metal spillage, since the tip element 23 is composed of a mixture of powdered metal (may be tungsten, copper, tantalum or brass, to name just some examples) and a synthetic plastic binder for the same (again, to name some examples, the binder may be polyurethane, silicone, polyvinylchloride or polyphosphazene). What is important in connection with the binder is that it be polymerizable, since after the mixture of metal powder and binder has been shaped to the desired form (see FIG. 2) it is subjected to polymerization in order to convert it into a unitary body. In this body the interstices between the metal-powder particles are filled by the synthetic plastic binder, and the polymerization unifies both materials into a whole. There is, therefore, no metal present that could leak or spill because none of the metal in element 23 is "loose" in the sense in which this is true in the prior art (as explained above with respect to FIG. 1).

The element 23 is secured to the tube 20 without any need for a connector, such as the one designated with reference numeral 7 in FIG. 1. Instead, in FIG. 2 the outer circumference of element 23 is recessed at the trailing end portion of the element, to form an annular groove 27, and the leading end portion 28 of the tube 20 is slipped into this groove 27 over the trailing end portion of element 23, as shown, and secured thereto in any well-known manner. This may be adhesively, by means of shrink-fit, heat-bonding or the like. It is also possible to provide the contacting surfaces of the trailing and leading end portions with respective inter-engaging formations (e.g. one or more circumferential beads and corresponding grooves to receive those beads; cooperating projections and depressions, or the like). These could then serve by themselves to maintain the elements 20 and 23 connected, or they could be used in conjunction with the adhesive or other connecting means mentioned above.

The exterior and/or interior of the element 23 may be provided with a layer or coating 29 (only one shown for the exterior) of any known-per-se material that prevents "leaching" of the metal forming part of the element 23, e.g. under the influence of a patient's stomach fluids. The layer 29 may, however, also be a layer of any known-per-se hydrophilic material in order to facilitate insertion of the element 23 into and through a body cavity. Of course, a hydrophilic coating will be needed, if at all, only on the outside of the element 23. It may itself prevent metal leaching, or it may be placed over a layer of anti-leaching material. No matter what is or is not used on the outside of the element 23, an anti-leaching layer may, if desired, always be placed on the inner surface bounding the lumen 24.

Figure 3:
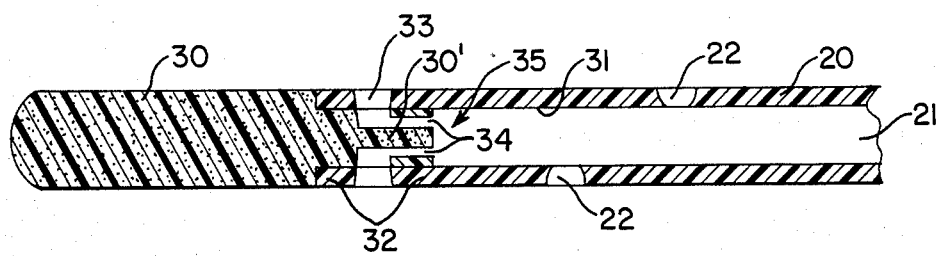
FIG. 3 is a sectional view analogous to that in FIG. 3 but showing a further embodiment of the invention.

FIG. 3 shows an embodimemt in which the tube, its lumen and the (again optional) openings in the tube have the same reference numerals as in FIG. 2. However, in its other aspects, the device of FIG. 3 is considerably different from the device of FIG. 2 in that the tip element 30 is of solid cross-sectional area. In other words: tip element 30 has no lumen. It is constructed in the same manner as the element 23; i.e. it is a unitary body of metal-powder particles embedded in a polymerized synthetic plastic binder. As such, it eliminates the metal spillage problem in the same manner as the element 23 does in the device of FIG. 2.

Given the absence of a lumen in the element 30, a problem of the FIG. 3 embodiment is, of course, how to avoid the formation of the undesirable stagnant pool of flowable substance which is so objectionable in the prior art. This problem is solved in the embodiment of FIG. 3 in that the trailing end portion 30' of element 30 and the leading end portion 32 of tube 20 overlap again in the same manner as in FIG. 2, except that in FIG. 3 the overlap may be somewhat greater in its axial extent than in FIG. 2. Formed in this area of overlap are outlet openings 33 which penetrate the leading end portion 32 of tube 20 and in part penetrate into the trailing end portion 30' of element 30. These openings communicate with recesses, grooves, bores or the like which have open ends 34 at the trailing end face 35 of the end portion 30' so that the lumen 21 of tube 20 is in direct communication with the openings 33 and outflow of the flowable substance can proceed unhindered through the openings 33. It goes without saying, of course, that other possibilities also exist for bringing about this result in generally the same manner. For example, the trailing end portion 30' could simply be of a lesser diameter than the remainder of element 30, i.e. have a circumferential recess rearwardly of the recess forming the step in which the front part of the leading tube end portion 32 is received. The openings 33 would then only have to be formed in the leading tube end portion 32 and communicate with this recess. Such a modification presupposes, however, that the tube will be mechanically resistant enough not to collapse to an extent that would block the flow of fluid to the openings 33.

Figure 4:
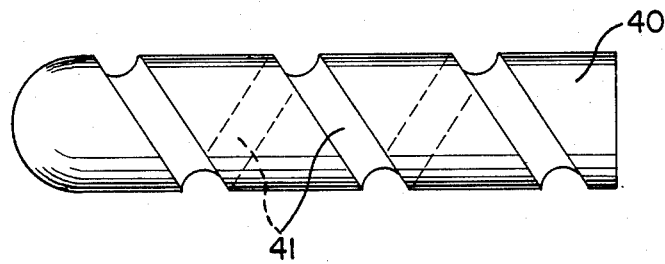
FIG. 4 is a longitudinal section through a tip element according to the invention, which embodies still further inventive concepts.

As previously pointed out, enhanced flexibility of the tip element is desirable over what is known from—and possible in—the prior art. FIG. 4 shows one of several ways in which this can be done with a tip element according to the present invention.

The tip element is identified in FIG. 4 with reference numeral 40 and is again a unitary body composed from a mixture of metal powder and polymerized synthetic plastic binder. As such, the tip element will in all embodiments of the invention already have a degree of flexibility that is superior to the prior art. This can be further improved, however, by providing the element 40 with one or more weakened zones in which it can more readily flex than elsewhere. In FIG. 4 these weakened zones are illustrated as a helical groove 41 which is incised (or formed during molding or casting) in the outer circumferential surface of the element 40; this groove may extend over any desired axial length of element 40 and may have different depths, all in dependence upon the degree of flexibility that is desired. Naturally, the helical groove is not the only way of providing a flexibility-enhancing zone. This could also be accomplished by, for example, forming or providing the element 40 instead with one or more annular circumferential grooves, with one or more axially elongated and circumferentially slanted grooves, or the like. Although the flexibility-enhancing feature will evidently be primarily applicable in the case of a solid cross-section tip element, it can also be used in the type of tip element shown in FIG. 2, i.e. one having a lumen.

The embodiments illustrated by way of explanation in the drawing will be recognized as being exemplary in nature, and not restrictive to the illustrated features. Various modifications can be made. For example, the leading end portion of the tube could be slipped inside the lumen of the trailing end portion of the tip element, rather than vice versa. If the circumferential wall of the tip element is thick enough in radial direction—or in the case of a solid cross-section tip element—the rear end face of the tip element could be provided with an annular groove into which the leading end of the tube is inserted and in which this leading end is anchored.

Figure 5:
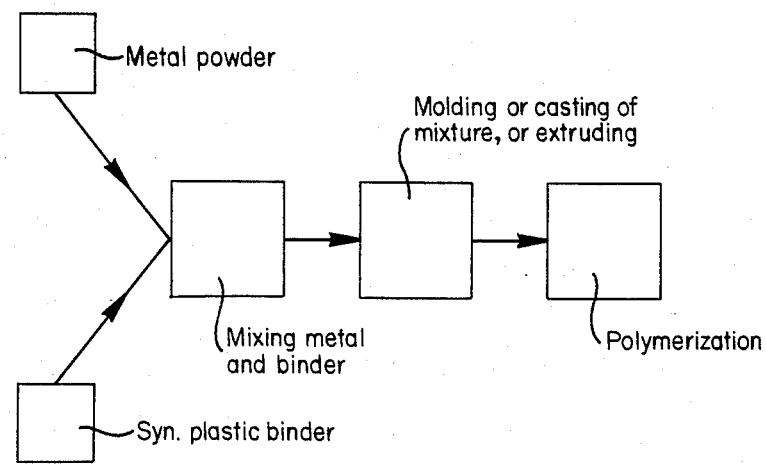
FIG. 5 is a flow diagram, showing basic steps involved in executing the method of the invention.

FIG. 5 shows some of the basic steps involved in carrying out the method according to the invention. The metal powder and the synthetic plastic binder are kept in separate supplies or reservoirs, from which they are advanced in any manner known per se to a mixing station. At this station the metal and binder are intimately mixed together and the resulting mixture is then introduced into another working station where it is shaped (by molding or casting, or even by extrusion) to form an elongated body of tubular or of solid cross-section. This body is then advanced to still another working station where it is subjected to polymerization, so that all the free metal in the body is now intimately bound with the binder and a unitary element results which has no free metal in it and from which no metal can consequently spill. All advancements, the shaping and the polymerizing according to the invention, can be carried out as known per se.

Figure 6:
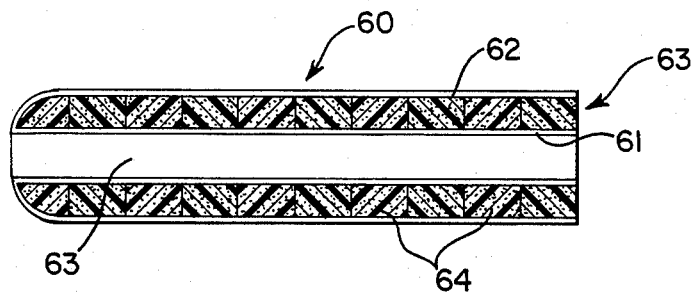
FIG. 6 is a view generally similar to that in FIG. 4, but with portions omitted, showing still another embodiment of the invention.

In the embodiment of FIG. 6 only the tip element 60 is shown; it will, of course, cooperate with an element 20 as in the preceeding embodiments. Here, the element 60 is of double-walled construction, having an inner and an outer wall 61 and 62, respectively (both shown only diagrammatically) which define between themselves an elongated annular clearance 63. Walls 61, 62 may be of any suitable and known-per-se synethetic plastic material. The inner wall 61 surrounds and defines a central passage or lumen 63 for the medium to be dispensed to the patient.

The weighting of the element 60 is accomplished, as illustrated, by confining in the clearance 63 a series of axially adjacent annuli 64. There may be made from the metal-powder/binder mixture disclosed herein and polymerized as discussed hereinbefore. In fact, that is what is shown in the drawing. However, it is also possible to simply use cut-offs from a section of tubing of a materal having the desired weight, since the annuli 64 are sealed and totally confined in the clearance 63 so that spillage or other metal release is not a problem. Also, the annuli 64 could be replaced with a continuous tubular body, either of tubing composed of a material having the desired weight or of the herein disclosed polymerized mixture of metal powder and binder.

Figure 7:
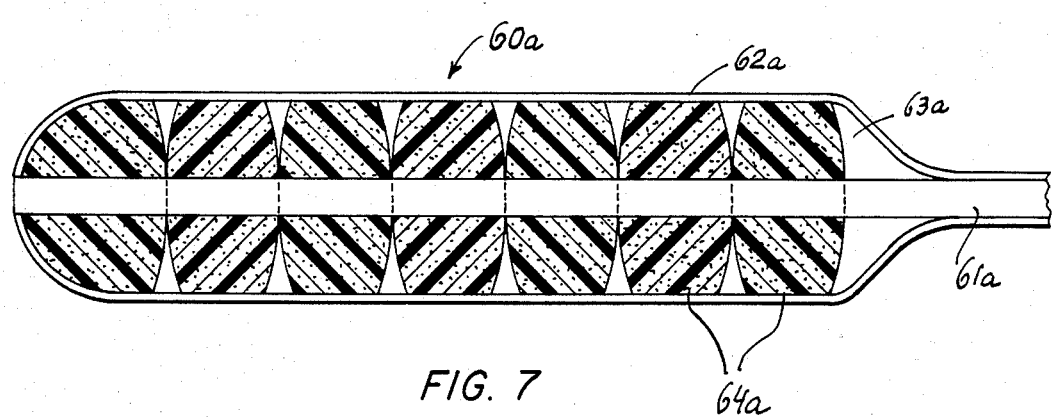
FIG. 7 is a fragmentary longitudinal sectional view of an additional embodiment of the invention.

A modification of the element 60 is shown in FIG. 7. The modified element 60a has an inner wall 61a, an outer wall 62a, an elongated annular clearance 63a between the walls 61a and 62a, and a set of normally coaxial tubular elements or annuli 64a in the clearance 63a. The neighboring surfaces of the annuli 64a are convex so as to promote the flexibility of the element 60a. The material of the tubular elements 64a may be identical with that of the elements 64 shown in FIG. 6. Thus, such material may be a metal-powder/binder mixture which is polymerized in a manner as described in connection with FIG. 5.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the claims.

We claim:

1. A medical device, particularly a catheter or feed tube, comprising a tube having a passage and being provided with a trailing end portion adapted to receive a flowable substance and a leading end portion; weighting means at said leading end portion and comprising an element composed of a mixture of powdered metal and synthetic plastic binder therefor, said element having two spaced ends and a channel which is open at said ends and communicates with said passage so that the flowable substance can pass from said tube into and through said element without hindrance; and outlet means for egress of flowable substance from said passage of said tube.

2. A device as defined in claim 1, wherein said tube is of synthetic plastic material.

3. A device as defined in claim 1, wherein said tube is of at least translucent synthetic plastic material.

4. A device as defined in claim 1, wherein said channel has a cross-sectional area which is at least equal to the cross-sectional area of said passage.

5. A device as defined in claim 1, wherein said metal is selected from the group consisting of tungsten, copper, tantalum and brass.

6. A device as defined in claim 1, wherein said binder is selected from the group consisting of polyurethane, silicone, polyvinyl chloride and polyphosphazene.

7. A device as defined in claim 1, wherein said element is at least somewhat flexible.

8. A device as defined in claim 1 wherein said element is elongated and further comprising covering means covering and surrounding said element over at least part of the elongation thereof.

9. A device as defined in claim 8, said covering means comprising a portion of said tube.

10. A device as defined in claim 8, said covering means comprising a sheath of medically inert material.

11. A device as claimed in claim 1, and further comprising a hydrophilic coating on said element for facilitating introduction thereof into body orifices and the like.

12. A device as defined in claim 1, wherein said element is at least in part radio-opaque so that is may be radiation-imaged to determine its position and orientation when the device is installed in situ.

13. A medical device, particularly a catheter or feed tube, comprising a tube having a passage and being provided with a trailing end portion adapted to receive a flowable substance, and a leading end portion; weighting means at said leading end portion and comprising an element composed of a mixture of powdered metal and synthetic plastic binder therefor, said element having two spaced ends and a channel which is open at said ends and communicates with said passage; and outlet means for egress of flowable substance from said passage of said tube, said outlet means comprising at least one opening in said tube and communicating with said passage rearwardly but in the vicinity of that one of said ends which in turn also communicates with said passage.

14. A device as defined in claim 13, wherein said channel and said tube have respective proximal end portions one of which is slipped over and surrounds the other so as to connect said element and tube to each other.

15. A device as defined in claim 1 and further comprising cooperating interengaging formations on said element and tube for connecting the element and tube to one another.

16. A weighted tip element, particularly for use with a medical device such as a catheter or feed tube, comprising an elongated unitary body composed of a mixture of synthetic plastic binder and metal powder interspersed therein, said body having a longitudinally extending channel provided with an open outlet end and an open inlet end; and means for securing said body to an end portion of a tube of a medical device so that said inlet end can communicate with the tube when said body is secured thereto.

17. An element as defined in claim 16, wherein said mixture is polymerized.

18. An element as defined in claim 16, wherein said body has a solid cross section, a circumferential surface and a rear end portion provided with a rear end face, said surface having at least one recess which is open thereat and at said rear end face.

19. An element as defined in claim 16, wherein said body have at least an outer circumferential surface, and further comprising a coating of antileaching material on said at least outer surface so as to prevent leaching of the metal in said body.

20. An element as defined in claim 16, wherein said body has at least an outer circumferential surface, and further comprising a coating of hydrophilic material on said at least one surface for facilitating the insertion of said element into a body orifice or the like.

21. An element as defined in claim 16, and further comprising means for enhancing the flexibility of said body transverse to said elongation thereof.

22. A weighted tip element, particularly for use with a medical device such as a catheter or feeding tube, comprising an elongated composite body including a tubular outer wall, an inner wall defining with said outer wall an elongated annular clearance, and a plurality of at least substantially coaxial annular members in said clearance; and means for securing said body to an end portion of a tube of a medical device.

23. A weighted tip element, particularly for use with a medical device such as a catheter or feeding tube, comprising an elongated composite body including a tubular outer wall, an inner wall defining with said outer wall an elongated annular clearance, and a plurality of at least substantially coaxial annular members in said clearance, said members being composed of a mixture of a synthetic plastic binder and a metallic powder interspersed in the binder; and means for securing said body to an end portion of a tube of a medical device.

24. An element as defined in claim 23, wherein said members have abutting end faces and at least substantially fill said clearance.

25. An element as defined in claim 23, wherein said inner wall is a tube.

26. An element as defined in claim 23, wherein at least some of said members have abutting neighboring convex surfaces and said walls are flexible to permit for flexing of said element.

* * * * *